(12) United States Patent
Tang

(10) Patent No.: US 9,352,157 B2
(45) Date of Patent: May 31, 2016

(54) INTRA-ORAL BALANCE DEVICE BASED ON PALATAL STIMULATION

(71) Applicant: Innervo Technology LLC, Columbia, MO (US)

(72) Inventor: Hui Tang, Columbia, MO (US)

(73) Assignee: Innervo Technology LLC, Columbia, MO (US)

( * ) Notice: Subject to any disclaimer, the term of this patent is extended or adjusted under 35 U.S.C. 154(b) by 0 days.

(21) Appl. No.: 14/387,304

(22) PCT Filed: Mar. 12, 2013

(86) PCT No.: PCT/US2013/030365
§ 371 (c)(1),
(2) Date: Sep. 23, 2014

(87) PCT Pub. No.: WO2013/172935
PCT Pub. Date: Nov. 21, 2013

(65) Prior Publication Data
US 2015/0057719 A1    Feb. 26, 2015

Related U.S. Application Data

(60) Provisional application No. 61/647,579, filed on May 16, 2012.

(51) Int. Cl.
*A61N 1/36* (2006.01)
*A61N 1/05* (2006.01)
*A61N 1/372* (2006.01)

(52) U.S. Cl.
CPC .......... *A61N 1/36139* (2013.01); *A61N 1/0548* (2013.01); *A61N 1/36067* (2013.01); *A61N 1/36171* (2013.01); *A61N 1/37235* (2013.01)

(58) Field of Classification Search
CPC ............ A61N 1/36139; A61N 1/0548; A61N 1/36067; A61N 1/36171; A61N 1/37235; A61N 2005/0606
USPC ........................................................ 607/134
See application file for complete search history.

(56) References Cited

U.S. PATENT DOCUMENTS

| | | | |
|---|---|---|---|
| 5,507,638 | A | 4/1996 | Strazielle |
| 5,807,284 | A | 9/1998 | Foxlin |
| 6,162,191 | A | 12/2000 | Foxlin |
| 6,546,291 | B2 | 4/2003 | Merfeld et al. |
| 8,092,398 | B2 | 1/2012 | Weinberg et al. |
| 2005/0267549 | A1 | 12/2005 | Della Saantina et al. |

(Continued)

*Primary Examiner* — Paula J Stice
(74) *Attorney, Agent, or Firm* — Raymond Sun

(57) ABSTRACT

A device for vestibular substitution includes a mouthpiece fitting entirely within a person's mouth in a shape that conforms to the palate. The mouthpiece encases a circuit board containing an electronic system that can deliver electrical pulses to electrical stimulators touching the palate based on head movement. The electronic system includes a motion sensor, a control unit; a stimulation circuit; and a battery. The control unit is preferably a microcontroller with a digital Input/Output capability, a Serial Peripheral Interface/Inter-Integrated Circuit protocol, a timer, and an oscillator for sensor interfacing and timing control. The microcontroller enables processing data from the accelerometer to indicate head movement, and controlling each embedded electrical stimulator to deliver electrical pulses with adjustable waveform parameters. The device may also include a wireless transceiver for remote control of the device from outside the person's mouth.

8 Claims, 4 Drawing Sheets

(56) References Cited

U.S. PATENT DOCUMENTS

| | | |
|---|---|---|
| 2007/0032748 A1 | 2/2007 | McNeil et al. |
| 2009/0306741 A1 * | 12/2009 | Hogle et al. .................. 607/54 |
| 2012/0022616 A1 | 1/2012 | Gamham et al. |

\* cited by examiner

INTRA-ORAL BALANCE DEVICE BASED ON PALATAL STIMULATION

CROSS-REFERENCE TO RELATED APPLICATIONS

This application claims the benefit of U.S. application Ser. No. 61/647,579, filed 16 May 2012, which is hereby incorporated by reference herein.

TECHNICAL FIELD

A device permits an individual with vestibular loss to evaluate his/her physical orientation by translating movement of the person's head to electrical stimulation that can be perceived as feedback thereby enabling the person to regain a sense of balance.

BACKGROUND ART

Vestibular imbalance is a serious problem due to loss of vestibular feedback resulted from various vestibular disorders. A vestibular rehabilitation therapy may alleviate the problem for some patients through regular training so that the brain can adapt to the vestibular loss with compensation from vision and proprioception. However, lost vestibular function cannot be fully compensated by visual and somatosensory cues, and the adaptation process may take months or years, and sometimes the adaption process may never be completed. Patients may become overly reliant on vision and proprioceptive senses, and postual instability often worsens when vision references are not reliable, or walking on uneven surfaces.

Various devices used to provide a prosthetic balance function may be implantable or non-implantable. The implantable stimulators are invasive and typically require surgical operations to be embedded under a patient's skin, such as within the ear canal in order to provide direct stimulation of the vestibular system.

Non-implantable prostheses are typically externally applied to the skin and thus are a much less invasive means of providing self-motion feedback. Such prostheses operate by, for example, stimulating the vestibular nerve via surface electrodes or by displaying self-motion cues using "sensory substitution," for example by acoustic indications, vibrotactile feedback, or electric currents applied to the tongue.

Typically, tactile vibrators are mounted on the subject's torso. A vibrotactile system typically involves an array of small electromechanical vibrators distributed on the torso or mounted on the head.

Alternative sensory feedback is provided through electrotactile stimulation of the tongue. A tongue input device developed by Wicab Inc. consists of a popsicle-like electrode array placed inside the mouth and a controller hanging in front of the chest with a cable running in between.

With electrotactile stimulation of the tongue, cosmetic appearance is a big issue. Head movement and speech are restricted. Patients would rather use it for rehabilitative training in a private setting.

Relatively large but wearable motion sensing vestibular prostheses have been developed to fit around a person's torso. These are capable of providing a subject with information concerning tilt and sway in multiple axes and can be equipped with an "air bag" to deploy upon a user falling.

SUMMARY OF INVENTION

A device for vestibular substitution includes a mouthpiece fitting entirely within a person's mouth in a shape that conforms to the palate or roof of the mouth. The mouthpiece encases a circuit board hosting an electronic system operable to deliver electrical pulses to stimulators touching the palate based on head movement. The electronic system includes a motion sensor, a control unit; a stimulation circuit; and a battery. The motion sensor is preferably an accelerometer. The control unit is preferably a microcontroller with a digital InputOutput capability, a Serial Peripheral InterfaceInter-Integrated Circuit protocol, a timer, and an oscillator for sensor interfacing and timing control. The microcontroller preferably has instructions coded in memory which enable processing data from the accelerometer to indicate head movement, and controlling each embedded electrical stimulator to deliver electrical pulses with adjustable waveform parameters. The device may also include a wireless transceiver for remote control of the device from outside the person's mouth. The stimulation circuit provides charge-balanced stimulation in the form of a voltage-controlled monophasic electric pulses with no net direct current. The control unit preferably uses pulse frequency modulation in which a higher magnitude of acceleration is indicated by a higher frequency of electric pulses.

Technical Problem

No existing non-implantable device for vestibular substitution is practical for patients to discretely use in various indoor and outdoor activities, due to inherent limitations associated with size, visibility of the prosthesis, awkwardness of the components, and interference with other bodily functions.

Major problems with auditory feedback in non-clinical settings are that it uses a sense that is already heavily loaded, and it can impede speech communication and block perception of environmental sounds that are equally important in indoor and outdoor activities. Or otherwise, noises in the surroundings may introduce false feedback that triggers imbalance.

Problems associated with vibrotactile feedback systems include power consumption and consequent fast battery depletion, large system size, heavy component weight, lack of ease of use, and an undesirable cosmetic appearance.

For devices using electrotactile stimulation of the tongue, cosmetic appearance is a big issue. Head movement and speech are restricted. Patients using the device typically go through regular training sessions in a private setting, and then rely on the residue effect of rehabilitative training for improved balance with no training devices worn. Statistically, the effectiveness of the residue effect derived from device training is not distinguishable from that of a rehabilitative training therapy.

Solution to Problem

A hidden device that can provide in-situ sensory feedback would be very desirable for vestibular substitution in indoor and outdoor activities, as vestibular feedback is an in-situ mechanism. With such a device, vestibular patients can have balance assistance when they need it the most.

Advantageous Effects of Invention

The palate-based device is completely hidden inside the oral cavity, and therefore, the cosmetic appearance of a patient is unaltered. It provides accurate detection of head acceleration as it is immobilized adjacent to a bone structure that is an integral part of the skull. It is a stand-alone device powered by a mini battery, with no wired electrical connection to external components. It provides for reliable stimulation delivered through stimulators that are in constant contact with the roof of the mouth, to wit, the palatal surface, a site that has been shown to possess high sensitivity to electrotactile stimulation, but has not been utilized for vestibular substitution.

Compared with vibrotactile feedback, the palatal device is miniature and energy efficient, making it more suitable for mobile use. Compared with auditory feedback, the device is silent and does not block speech and environmental sound that are equally important during indoor and outdoor activities. It is useful for patients with both vestibular and auditory impairments. In addition, the device allows free movement of the head and talking.

BRIEF DESCRIPTION OF DRAWINGS

The drawings illustrate preferred embodiments of the method of the invention and the reference numbers in the drawings are used consistently throughout. New reference numbers in FIG. 2 are given the 200 series numbers. Similarly, new reference numbers in each succeeding drawing are given a corresponding series number beginning with the figure number.

DESCRIPTION OF EMBODIMENTS

In the following description, reference is made to the accompanying drawings, which form a part hereof and which illustrate several embodiments of the present invention. The drawings and the preferred embodiments of the invention are presented with the understanding that the present invention is susceptible of embodiments in many different forms and, therefore, other embodiments may be utilized and structural, and operational changes may be made, without departing from the scope of the present invention.

Any exemplary embodiment of the palate-based balance device may be referred to herein as a palatal device because it is affixed against the palate in a person's mouth. For purposes herein, the palate is the roof of the mouth that spans the arch formed by the upper teeth. Preferred embodiments are removably worn in a person's mouth against the palate, that is physically in contact with the roof of the mouth and are not implanted into the skin or bone.

Any exemplary embodiment of the palate-based balance device may also be described as a prosthesis for vestibular substitution for use within a person's mouth because even though it is within the oral cavity, it functions as a prosthesis that substitutes for the vestibular organ inside the inner ear when a person has a malfunctioning or impaired balance system. This device may also be described as a mouthpiece because it fits and is worn entirely within a person's mouth.

Figure 1:
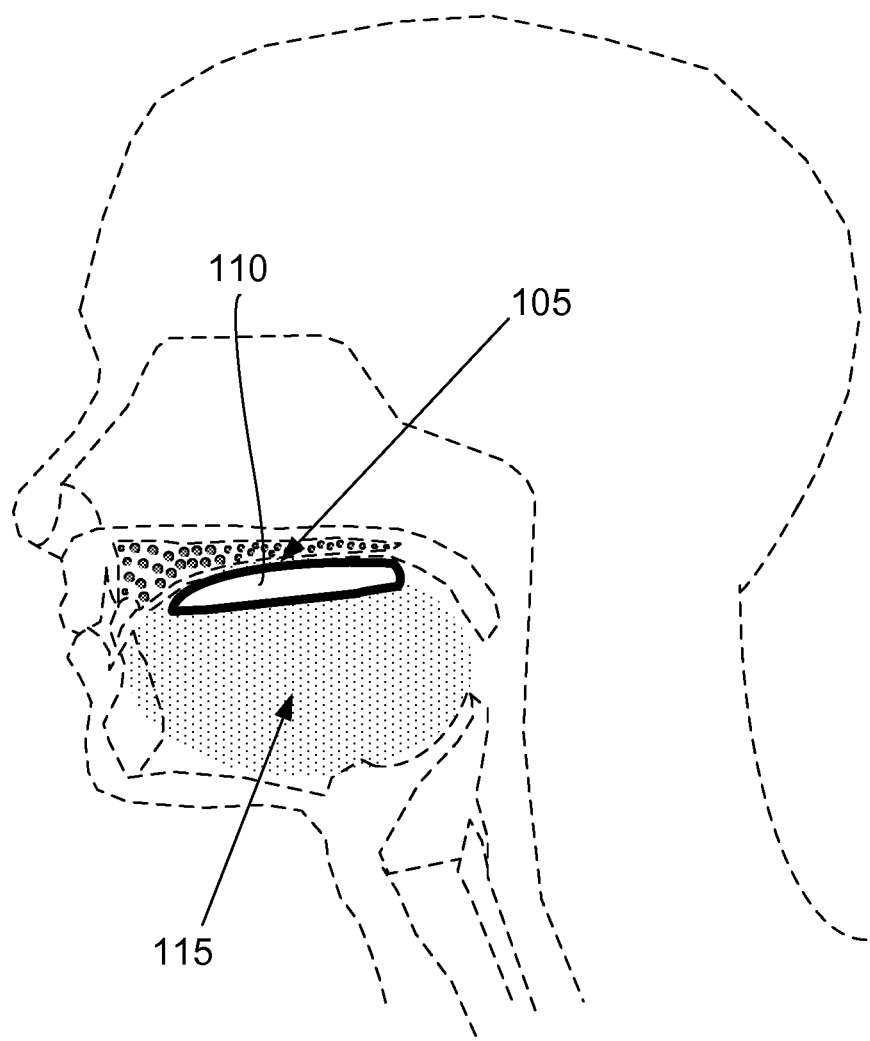
FIG. 1 shows a palate-based balance device in position inside a person's mouth.

FIG. 1 shows a preferred embodiment of the device for vestibular substitution within a person's oral cavity, or mouth (115). The device includes a mouthpiece (110) configured to conform to the roof (105) of the mouth (115). Preferably, each such device would be made to conform to the person who would be using it. Typically, it would be made using a mold of the person's mouth so that it would precisely fit that person. The mouthpiece may optionally be a mouth impression, a dental retainer, or a metal frame structure. In some embodiments, the palatal device may be made to feel like an "artificial hard palate" for the user. The mouthpiece (110) is preferably made of dental acrylic, which serves as a supporting material for the mouthpiece (110). Alternative embodiments may use silicone impression to make the mouthpiece (110), or may use a frame structure (for example, made from metal wires) for holding the mouthpiece against the roof (105). A mouthpiece (110) in exemplary form is about 5 centimeters long, and 3.8 centimeters wide at the midsection, recognizing that these dimensions will change for different individuals.

The mouthpiece (110) houses the components of the device. The first such component is a circuit board (301), illustrated in FIG. 3. The circuit board (301) is encased within the mouthpiece (110). The circuit board (301) holds or defines an electronic system (300) capable of operation wholly within itself and without wired connection external to the mouth (115). This means that for normal operability of the device, there are no wires or other parts that are visually present to connect between the mouthpiece (110) and any components outside the mouth (115). The electronic system (300) includes a motion sensor (305), a control unit (315), a stimulation circuit (325), and a battery (330). In preferred embodiments, the circuit board (301) is a mini circuit board with rounded front and having dimensions no larger than about 2×3 centimeters, and the battery is preferably coin battery with a potential difference of about 3 volts.

The electronic system (300) detects head movement, preferably using acceleration sensing, and provides alternative sensory feedback through electrotactile stimulation on the palate.

The mouthpiece (110) further includes a plurality of embedded electrical stimulators (210) which when the mouthpiece (110) is installed within the person's mouth, each embedded electrical stimulator in the plurality of embedded electrical stimulators (210) are in contact with the roof (105) of the mouth (115). A preferred number of embedded electrical stimulators (210) is four, but there may be more or less than four. For example, two stimulators might be used to indicate just two directions (e.g., left or right). More than one stimulator may also be used for each direction.

The plurality of embedded electrical stimulators (210) is connected to the electronic system (300) such that each embedded electrical stimulator in the plurality of embedded electrical stimulators (210) can receive an electrical pulse (446) from the electronic system (300) and transmit the electrical pulse (446) to the roof (105) of the mouth (115). In order to transmit the electrical pulse (446) to the roof (105), there is preferably a return electrode (215), also referred to as a counter electrode, that completes an electrical circuit.

Because the circuit board (301) is encased within the mouthpiece (110), all of the operable components are also preferably fully encased within the mouthpiece (110), except that each embedded electrical stimulator in the plurality of embedded electrical stimulators (210) preferably protrudes from the mouthpiece (110) in order to enable each of them to send electrical current to the roof (105) of the mouth (115). In alternative embodiments, one or all of the embedded electrical stimulators in the plurality of embedded electrical stimulators (210) are fully encased within the mouthpiece (110) and the electric charge is conveyed through the external surface of the mouthpiece (110) to the roof (105) of the mouth (115).

The motion sensor (305) within the electronic system (300) is typically an accelerometer, which may be used alone or in combination with other motion sensors, such as a gyroscope. The term "motion sensor" is intended to refer to a sensor or sensors of any kind that can detect movement, such as for example, position, velocity, acceleration, or rotation.

The control unit (315) within the electronic system (300) is typically a microcontroller that includes on-chip peripherals enabling operability. These on-chip peripherals include a digital InputOutput (318) capability; a Serial Peripheral InterfaceInter-Integrated Circuit protocol (316), often abbreviated as SPI/I2C digital interface; a timer (319); and an oscillator (320) for sensor interfacing and timing control. The control unit determines the direction of head motion based on the data from the motion sensor and turns on/off the corresponding stimulator(s) accordingly. Alternatively, a microcontroller can have an analog to digital (A/D) converter that accepts analog input from the motion sensor.

The microcontroller preferably includes instructions encoded on non-transitory storage (321), such as for example random access memory, read-only memory, and other semiconductor memory devices, such as EEPROM, and flash memory devices. The instructions when implemented execute steps of processing data from the motion sensors, such as the accelerometer, to indicate head movement, and controlling each embedded electrical stimulator to deliver an electrical pulse (446) or pulses with adjustable waveform parameters. The electrical pulse (446) creates a "tickling" sensation on the palate at the stimulator location that corresponds to the direction of tilting or movement of the mouthpiece, and thus the head. Thus, the electrical pulse (446) provides alternative sensory feedback of head movement.

The stimulation circuit (325) generates charge-balanced stimulation in the form of electric pulses with no net direct current. The electric pulses may be voltage-controlled or current-controlled, monophasic or biphasic. The control unit (315) preferably uses pulse frequency modulation in which a higher magnitude of acceleration is indicated by a higher frequency of electric pulses.

Figure 3:
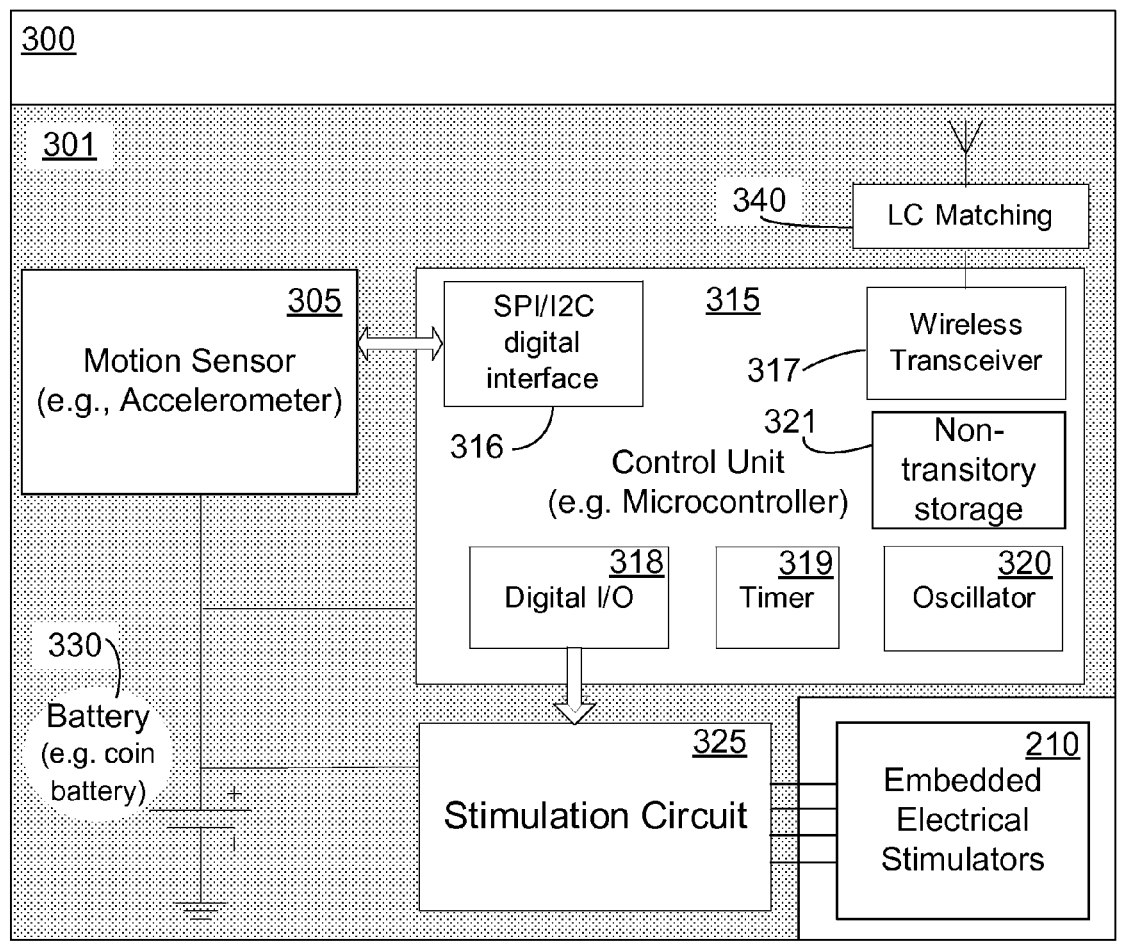
FIG. 3 is a system diagram of an exemplary microcontroller-based electronic system within the mouthpiece.

The device for vestibular substitution may also include a wireless transceiver (317) within the mouthpiece (110). The wireless transceiver (317) enables remote control of the device from outside the person's mouth. The wireless transceiver (317) would receive control instructions from a remote controller. For example, the control instructions received by the wireless transceiver (317) might command the control unit (315) to adjust the intensity of electrical pulses or turn the electronic system (300) on or off. In FIG. 3, LC Matching (340) refers to a network of inductor-capacitor (LC) components that match the impedance between the radio-frequency (RF) end of the wireless transceiver and the antenna (indicated by the vertical line with two arms extending from the box around LC Matching (340).

Example 1

Four-Stimulator Configuration

Figure 2:
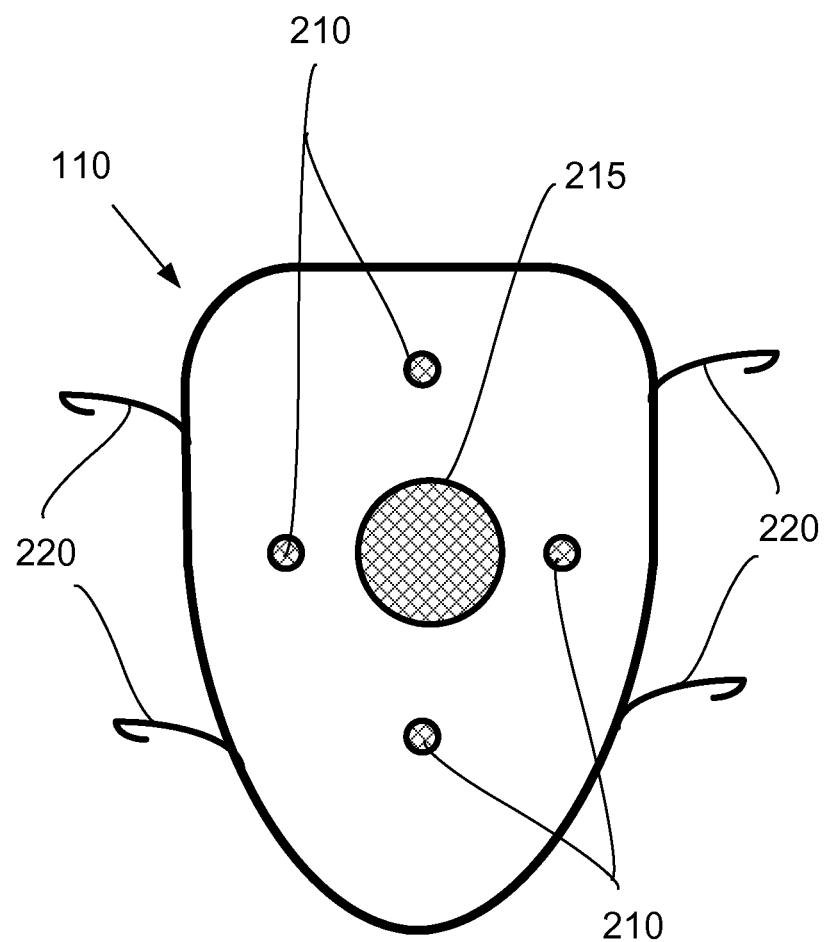
FIG. 2 is a top view of the device, also referred to herein as a mouthpiece, illustrating an exemplary distribution of stimulators embedded within the mouthpiece.

A preferred embodiment, shown in FIG. 2, has a four-stimulator configuration that facilitates a compact and energy-efficient implementation of the electronic system while allowing presentation of the direction as well as the range of head movement using electrotactile stimulation. The sensory feedback regarding head movement is represented by small electrical pulse trains delivered through the stimulators. The range information is coded into the waveform parameters of the stimuli that can be perceived as having varying sensory characteristics. Specifically, frequency encoding is used to indicate the magnitude of the movement. The implementation allows the entire device to be powered by a mini battery, such as a coin battery, while generating adequate intensities for strong and comfortable sensations on the palate.

The electronic system is assembled into a mini circuit board that is embedded in a dental retainer. In this example the dental retainer is a mouthpiece with metal wireclips (220) that wrap around the upper teeth to hold the device against the palate. A mechanical bracing provided by a dental retainer is a preferred means for fixing the mouthpiece in place against the retainer. Glue or other securing means are also possible. As shown in FIG. 2, there are four embedded electrical stimulators, also referred to as stimulators. The stimulators in this example are symmetrically distributed on top of the mouthpiece (110) with the return electrode (215) at the center. Two stimulators are located laterally with respect to the vertical centerline to indicate head movements in lateral directions, while the other two stimulators are used to indicate movement in the posterior-anterior direction. Head movement is indicated by localized stimulation applied to the nerve endings on the primary regions of the palatal surface, namely, the left and right branches of the palatine nerve, and the nasopalatine nerve. Stimulators in this example are slightly raised electrodes, that is, electrodes that protrude from the surface of the mouthpiece. These electrodes are coated with a noble metal to minimize any potential irreversible electrochemical reactions at the device-tissue interface while delivering stimulating pulses generated from the electronic system (300).

Example 2

Microcontroller-Based Electronic System

A preferred embodiment includes an electronic system (300) that has a microcontroller, an accelerometer chip, and a stimulation circuit, as shown in FIG. 3. The electronic system (300) is powered by a coin battery while generating adequate intensities for strong and comfortable sensations on the palate. The microcontroller has on-chip peripherals including digital IO, SPI/I$^2$C interface, timers, and oscillators for sensor interfacing and timing control. The microcontroller is programmed to process data from the accelerometer, which indicates head movement, and controls the stimulators to deliver electrical pulses with adjustable waveform parameters. Use of surface-mount components allows compact integration of the microcontroller-based system onto a mini circuit board. This exemplary system includes wireless communication capability for remote control of the device from outside.

In other embodiments, the electronic system may be a printed circuit board, or flexible printed circuits. Part or whole of the entire electronic system may be made using application-specific integrated circuits so that the device can be further miniaturized.

Example 3

Charge-Balanced Stimulation

Figure 4:
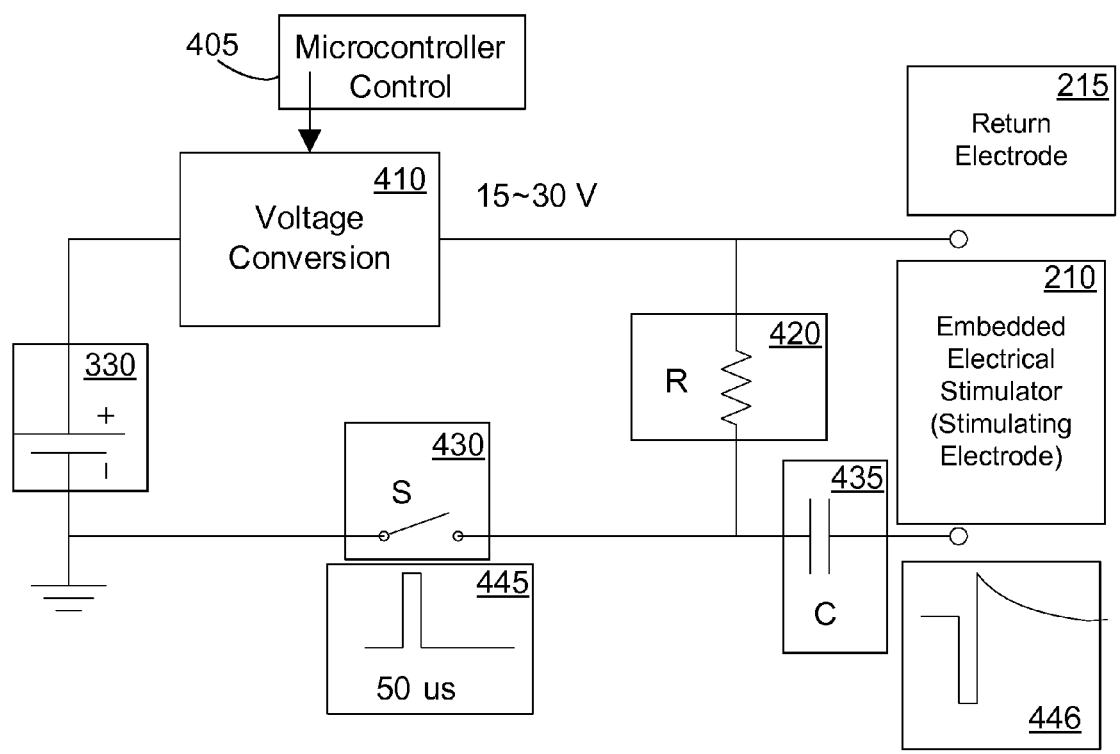
FIG. 4 is a circuit diagram illustrating functions in generating charge-balanced stimulation for a stimulating electrode.

The stimulation circuit (325) in this example provides charge-balanced stimulation in the form of voltage-controlled monophasic pulses with no net DC current. The stimulation circuit for one channel (one stimulator) is illustrated in FIG. 4. A control signal (445) from the control unit (315) causes switch S (430) to momentarily close for a short duration, for example, 50 micro-seconds, during which negative charge is injected into the stimulating electrode (210), forming a cathodic phase of the stimulus pulse. The switch S (430) is then opened, and capacitor C (435) gradually discharges through resistor R (420) reversing the current flow so that the charge injected in the previous phase is slowly withdrawn. This control sequence can be repeated to produce a number of stimulating pulses. The stimulation circuit has voltage conversion (410) that converts the voltage from the battery into a voltage preferred for palatal stimulation (about 15-30 Volts), which is adjustable by another microcontroller control (405). A counter electrode, also called the return electrode (215), allows current to flow back and forth in the palatal tissue.

Example 4

Electrotactile Representation of Head Movement

In this example, four stimulators are utilized to present a two-dimensional acceleration vector in the medial-lateral plane, with two orthogonal components in x- and y-axis respectively. The sign of each component is indicated by localized stimulation on one of the four stimulators. The magnitude of that component is coded into the stimulation waveform by varying one of the waveform parameters used for that stimulator. This embodiment uses pulse frequency modulation in which a higher magnitude of acceleration is indicated by a higher frequency of the stimulus pulses.

In this example, pulse frequency is modulated according to different functions including:

Linear function: $f = c(|a_i| - A_{min}) + F_{min}$ and $c = (F_{max} - F_{min})/(A_{max} - A_{min})$.

Inverse tangent function: $f = \frac{2F_{max}}{\pi}\tan^{-1}\left[c(|a_i| - A_{min}) + \tan\left(\frac{\pi F_{min}}{2F_{max}}\right)\right]$.

Exponential function: $f = F_{max} - (F_{max} - F_{min})\exp[-c(|a_i| - A_{min})]$.

The linear function has constant sensitivity defined by c within the dynamic range of acceleration from $A_{min}$ to $A_{max}$, but higher sensitivity often correlates to a reduced dynamic range. Beyond that range, the pulse frequency is typically not responsive to the acceleration change. The inverse tangent function is nearly linear in the lower range of the acceleration, while keeping the pulse frequency responsive to acceleration change at the higher end. The exponential function typically has maximal sensitivity at the low end of the acceleration ($A_{min}$), and then decreases exponentially as acceleration increases. $A_{min}$ defines the no-feedback zone within which balance is considered maintained. The frequency can change in a range between $F_{min}$ and $F_{max}$, which should be chosen to enhance discrimination and perception by the brain, for example, between 2 Hz and 80 Hz.

Example 5

Presentation of Orthogonal Components

In this example, the microcontroller includes instructions coded on non-transitory storage, which when implemented execute preferred approaches to present the orthogonal components of the acceleration vector. These approaches include: 1) Singular activation. Only one of the four stimulators is activated at any moment, which always indicates the larger component of the acceleration vector. This method presents an easier task for human recognition. Either one of the two orthogonal components may become more significant as the individual attempts to make body adjustments. Only the more significant component is presented for human perception. 2) Dual activation. Two stimulators are activated simultaneously to represent both orthogonal components. The two activated stimulators may use different pulse frequencies. The approach of dual activation may present a more complicated task for the brain because it needs to discriminate these two stimuli, identify which component is more significant, and form a perception where the acceleration vector is pointing at.

The invention may have application to other uses. For example, if the motion sensor is mounted on an external object (such as an aircraft), and communicate with the intraoral device wirelessly, then the invention would be able to give the user feedback regarding the tilting or motion of the external object.

The above-described embodiments including the drawings are examples of the invention and merely provide illustrations of the invention. Other embodiments will be obvious to those skilled in the art. Thus, the scope of the invention is determined by the appended claims and their legal equivalents rather than by the examples given.

INDUSTRIAL APPLICABILITY

The invention has application to the medical industry.

What is claimed is:

1. A device for vestibular substitution for use within a person's mouth, the person's mouth comprising a roof of the mouth, the device configured to provide alternative sensory feedback of head movement through electrical stimulation on the roof of the mouth, the device comprising:
   a mouthpiece fitting entirely within the person's mouth, the mouthpiece configured to conform to the roof of the mouth, the mouthpiece comprising a circuit board encased therein, the circuit board defining an electronic system that, in an normal operation mode, generates electrical pulses automatically in response to head tilt and/or head movement without positioning any components outside of the person's mouth, the electronic system comprising:
   a motion sensor configured to detect head tilt or head movement;
   a control unit configured to generate pulse frequency modulation in which the magnitude of acceleration due to head tilt or head movement corresponds to the frequency of electric pulses;
   a stimulation circuit; and
   a battery;
   the mouthpiece further comprising a plurality of embedded electrical stimulators which when the mouthpiece is installed within the person's mouth, the embedded electrical stimulators are in contact with the roof of the mouth, and
   wherein the embedded electrical stimulators are connected to the electronic system such that each embedded electrical stimulator in the plurality of embedded electrical stimulators can receive the electrical pulses from the electronic system and transmit the electrical pulses to the roof of the mouth.

2. The device according to claim 1, wherein:
   the motion sensor comprises an accelerometer that measures the acceleration due to static head tilt and acceleration due to dynamic head movement; and
   the control unit comprises a microcontroller, the microcontroller comprising on-chip peripherals, the on-chip peripherals comprising a digital Input/Output capability; a Serial Peripheral Interface/Inter-Integrated Circuit protocol; a timer; and an oscillator for sensor interfacing and timing control;

the microcontroller further comprising instructions coded on non-transitory storage, the instructions which when implemented execute steps of processing data from the accelerometer to indicate head movement, and controlling one or more of the embedded electrical stimulators to deliver electrical pulses with adjustable waveform parameters.

3. The device according to claim 1, further comprising an external controller that allows a user to wirelessly interact with the intra-oral device for additional functions such as turning on/off the device or adjustment of device settings.

4. The device according to claim 1, wherein the electronic system wherein the stimulation circuit provides charge-balanced stimulation in the form of a voltage-controlled monophasic electric pulse with no net direct current.

5. The device according to claim 1, wherein the plurality of embedded electrical stimulators comprises four stimulators that are utilized to present a two-dimensional acceleration vector in the medial-lateral plane, with two orthogonal components in x- and y-axis respectively, wherein the sign of one component is indicated by localized stimulation on one of the four stimulators.

6. The device according to claim 5, wherein the magnitude of the acceleration component is coded into the stimulation waveform by varying the frequency of the pulses used for that stimulator.

7. The device according to claim 6, wherein a higher magnitude of the acceleration component is indicated by a higher frequency of electric pulses.

8. The device according to claim 6, wherein pulse frequency is modulated according to different functions including:

Linear function: $f = c(|a_i| - A_{min}) + F_{min}$ and $c = (F_{max} - F_{min})/(A_{max} - A_{min})$.

Inverse tangent function: $f = \frac{2F_{max}}{\pi}\tan^{-1}\left[c(|a_i| - A_{min}) + \tan\left(\frac{\pi F_{min}}{2F_{max}}\right)\right]$ Exponential function: $f = F_{max} - (F_{max} - F_{min})\exp[-c(|a_i| - A_{min})]$.

wherein the linear function has constant sensitivity defined by c within the dynamic range of acceleration from $A_{min}$ to $A_{max}$, the inverse tangent function is nearly linear in the lower range of the acceleration, while keeping the pulse frequency responsive to acceleration change at the higher end, the exponential function typically has maximal sensitivity at the low end of the acceleration ($A_{min}$), and then decreases exponentially as acceleration increases, and $A_{min}$ defines the no-feedback zone within which balance is considered maintained.

* * * * *